United States Patent
Lewicke (10) Patent No.: US 8,506,481 B2
(45) Date of Patent: *Aug. 13, 2013

(54) PATIENT MONITORING APPARATUS

(75) Inventor: John Lewicke, Mason, NH (US)

(73) Assignee: Nova Technology Corporation, Portsmith, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/302,244

(22) Filed: Nov. 22, 2011

(65) Prior Publication Data

US 2012/0065522 A1 Mar. 15, 2012

Related U.S. Application Data (63) Continuation of application No. 12/707,997, filed on Feb. 18, 2010, now abandoned, which is a continuation of application No. 11/161,688, filed on Aug. 12, 2005, now abandoned.

(60) Provisional application No. 60/601,243, filed on Aug. 13, 2004.

(51) Int. Cl.
*A61B 5/00* (2006.01)

(52) U.S. Cl.
USPC .......................................... 600/301; 600/323

(58) Field of Classification Search
None
See application file for complete search history.

(56) References Cited

U.S. PATENT DOCUMENTS

| | | | |
|---|---|---|---|
| 5,722,999 A * | 3/1998 | Snell | 607/32 |
| 6,203,493 B1 * | 3/2001 | Ben-Haim | 600/117 |
| 6,243,608 B1 * | 6/2001 | Pauly et al. | 607/60 |
| 6,544,173 B2 * | 4/2003 | West et al. | 600/300 |
| 6,790,178 B1 * | 9/2004 | Mault et al. | 600/300 |
| 7,647,237 B2 * | 1/2010 | Malave et al. | 705/3 |
| 2001/0044588 A1 * | 11/2001 | Mault | 600/549 |
| 2005/0197859 A1 * | 9/2005 | Wilson et al. | 705/2 |
| 2012/0065522 A1 * | 3/2012 | Lewicke | 600/476 |

* cited by examiner

*Primary Examiner* — Bill Thomson
*Assistant Examiner* — Shirley Jian
(74) *Attorney, Agent, or Firm* — George A Herbster (57) ABSTRACT

A patient monitoring system including a sensing-recording device that attaches to a patient and a probe utilized by attending personnel at a trauma site. After an initial interaction between the probe and the sensing-recording device, the sensing-recording device samples one or more physiological parameters and stores time stamped readings in a first memory. The probe is adapted to take other measurements, download the data from the first memory of the sensing-recording device, manipulate the collective data and return data to a second memory in the sensing-recording device. The sensing-recording device continues to accumulate data in the first memory during transport of the patient from a trauma, site to a medical facility.

13 Claims, 8 Drawing Sheets

PATIENT MONITORING APPARATUS

BACKGROUND OF THE INVENTION

1. Field of the Invention

This invention generally relates to monitoring physiological parameters of a patient and more specifically to the monitoring of such parameters in patients who are geographically remote from a medical facility.

2. Description of Related Art

Monitoring of a patient's physiological parameters in a medical environment is an important element of patient diagnosis and treatment. Within a modern medical facility, such as a hospital, such monitoring is relatively easy to perform. The environment is controlled. The staff, including physicians, nurses, physician assistants and technicians, is qualified. Such facilities have equipment resources for enabling the monitoring of one or more patients for a variety of physiological parameters.

Unfortunately the advantages of a hospital environment with its resources and personnel do not exist at many trauma sites, such as those at accident scenes or at battlefield sites. First responders to an accident scene generally include an emergency medical technician (EMT). The EMT assesses the patient and, in conjunction with advice from medical personnel established by radio contact, initiates treatment. Typically the EMT stays with the patient during transport to a medical facility. The EMT can transfer his or her observations to personnel at the facility by interview and/or by written record.

An entirely different situation exists on a battlefield. On a battlefield a medic is attached to a particular unit. The medic treats a patient. When the medic completes treatment at the battlefield site, the patient is transported to another facility. However, the medic stays behind to attend to other patients. The medic's initial treatment protocol will be based on certain readings taken at the site. Then there are procedures for identifying the actions that were taken at the site. For example, if a sedative is administered, the medic may pin the syringe to the patient. Typically no interview occurs between the personnel at the medical facility, such as a field hospital, and the attending medic. Moreover, typically no information is recorded about the patient during initial treatment and transport for transfer to the field hospital.

Recently proposals have been made for personal monitoring systems for use in a battlefield environment. U.S. Pat. No. 6,198,394 (2001) to Jacobsen et al. discloses one such system for remote monitoring of personnel. This system utilizes a harness with a number of sensors to be worn continuously by a soldier. The sensors monitor a number of parameters including physiological variables. The harness carries a transmitting unit for transferring data to a central site.

U.S. Pat. No. 6,454,708 (2002) to Ferguson et al. discloses a portable remote patient tele-monitoring system using a memory card or a smart card. This system includes a multi-parameter sensor array applied to a patient's chest by means of a sensor band. The smart card or memory card stores measured data. Alternatively, a data logger carried by the patient receives the data. A base station receives the recorded information and transmits it to a remote monitoring site over a telecommunications link. The sensor band is disposable and has a limited life. For long-term monitoring, sensor bands may be replaced periodically.

U.S. Patent Publication No. 2004/0147818 (2004) to Levy et al. discloses a portable system for monitoring and processing patient parameters in multiple operational modes. Specifically a data acquisition processor receives data from sensors on a patient and processes that data. The processed data is communicated to a docking station with a portable monitoring unit in one operational mode or to a network access point in a wireless network in another operational mode.

As will be apparent, each of these proposals requires the use of bulky equipment. The Jacobsen et al. patent requires a soldier to wear a harness to be worn at all times. First, such a requirement requires the soldier to carry extra weight and to take precautions to avoid damaging the equipment during normal use. It is not likely that such a harness would be an acceptable alternative for application to a trauma patient on a battlefield or at another trauma site. Such apparatus is bulky, so it would be difficult to inventory such harnesses for multiple patients. In addition, medical personnel would have the additional burden of placing the harness on a trauma patient under adverse circumstances.

Each of these systems depends upon the availability of sophisticated communications links, such as those available in a hospital environment. They are not always available at a trauma site or on the battlefield. The use of smart cards or memory cards as suggested in the Ferguson et al. patent present problems because such devices are prone to being lost at a trauma site or during patient transport to a hospital or other central site. Further, only the data-measured at the trauma site is recorded.

What is needed is patient monitoring apparatus that includes a compact sensor and recording device that medical personnel on the battlefield or at a trauma site can readily inventory and apply to a patient in a positive, secure manner for recording various physiological data. What is also needed is such apparatus that facilitates use by medical personnel and that provides a continuum of data for use by personnel at a hospital or like facility.

SUMMARY

Therefore it is an object of this invention to provide patient monitoring apparatus that is adapted for use in a variety of environments including battlefield environments.

Another object of this invention is to provide apparatus for monitoring certain physiological parameters of a patient from the arrival of a first responder or medic at a site to the arrival of the patient at a medical facility.

Yet another object of this invention is to provide patient monitoring apparatus that is easy to use and facilitates the measurement of physiological parameters.

In accordance with one aspect of this invention, sensing-recording device provides a history of a patient medical parameter to an output device. The sensing-recording device includes a housing that attaches to the patient. A sensor carried by the housing generates a signal that represents the medical parameter. A controller in the housing stores samples of the sensor output in a memory. A communications link enables the transfer of data from the memory to the output device.

In accordance with another aspect of this invention a patient monitoring apparatus includes a sensing-recording device and a probe. The probe can establish a communications path to the sensing-recording device. The probe comprises a memory, a processor for processing data in the memory and a probe controller for generating commands to and for storing data from a sensing-recording device over the communications path. The sensing-recording device comprises a housing that attaches to a patient. A sensor carried by the housing generates a signal that represents the medical parameter. A memory and a control in the housing store samples of the sensor output in the memory. The control responds to commands from the probe by transferring data in the memory to the probe.

In accordance with still another aspect of this invention, a patient monitoring system adapted for use by medical personnel at a trauma site comprises a plurality of sensing-recording devices and a probe. Each of the devices includes a housing that can be securely attached to a patient, a plurality of sensors, each of which generates a signal that represents a medical parameter, first and second memories, a controller for storing time-stamped data sample entries for each sensor in said first memory, a transceiver for establishing communications over an optical communications path wherein information from the transceiver is stored in the second memory. The probe includes a plurality of sensors, each sensor generating a signal that represents a medical parameter. a memory for storing time-stamped data entries representing samples of the signal from each sensor, a display, a processor for processing the data in the memory for viewing on the display, a keyboard, a probe operation control that processes one of a plurality of tasks in response to inputs from the keyboard, a transceiver for establishing communications over an optical communications path whereby data in the probe is conveyed to the second memory in the sensor-recording devices for a patient.

BRIEF DESCRIPTION OF THE DRAWINGS

The various objects, advantages and novel features of this invention will be more fully apparent from a reading of the following detailed description in conjunction with the accompanying drawings in which like reference numerals refer to like parts, and in which.

DESCRIPTION OF ILLUSTRATIVE EMBODIMENTS

Figure 1:
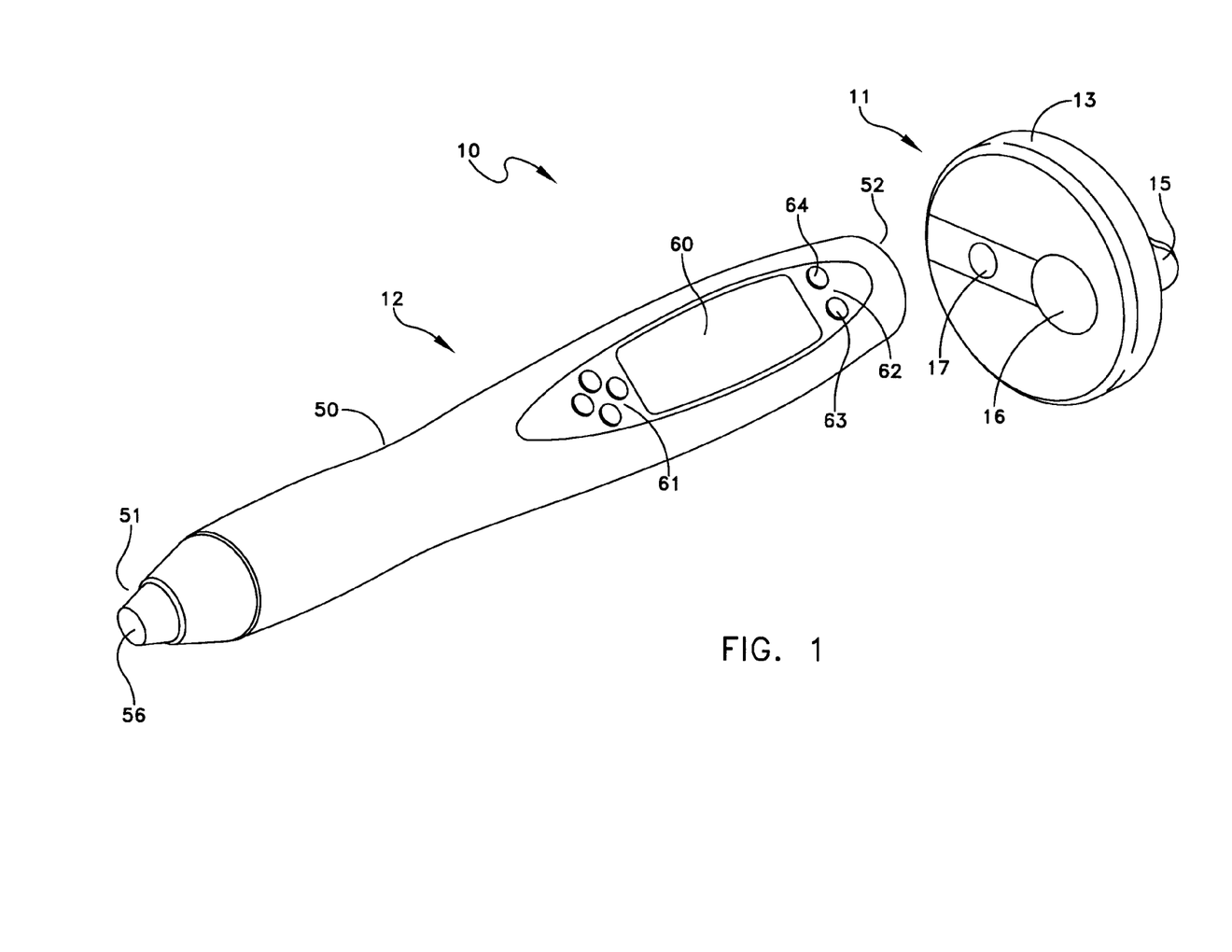
FIG. 1 depicts monitoring apparatus in accordance with this invention.

In FIG. 1 patient monitoring apparatus 10 includes a sensor button 11 that includes the capability of sensing a recording data related to a medical parameter, hereinafter a "sensing-recording device" and a probe 12. In use the sensing-recording device 11 is attached to a single patient. A medic will carry multiple sensing-recording devices and attach at least one sensing-recording device 11 to each patient. In the following discussion the term "medic" normally identifies military personnel; however, in conjunction with this invention the term includes both military personnel and civilian personnel such as an EMT. Each medic will also have a single probe 12. An individual probe 12 may be used in conjunction with multiple sensing-recording devices, such as the sensing-recording device 11, for multiple patients.

Sensing-Recording Device 11

Figure 2:
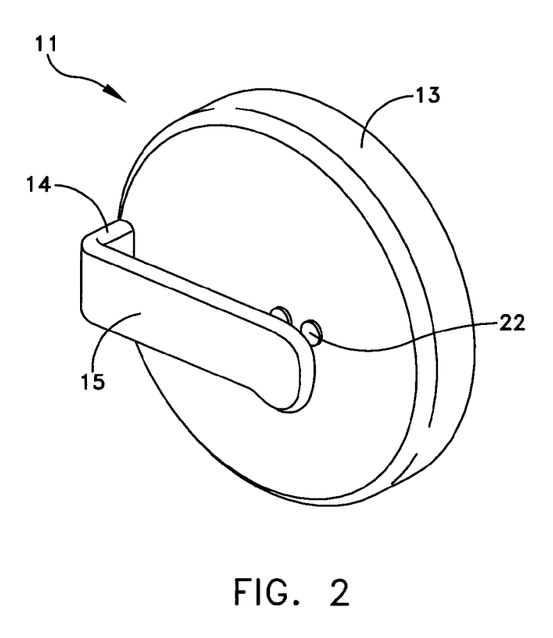
FIGS. 2 and 3 are different perspective views of a sensing-recording device shown in FIG. 1.
Figure 3:
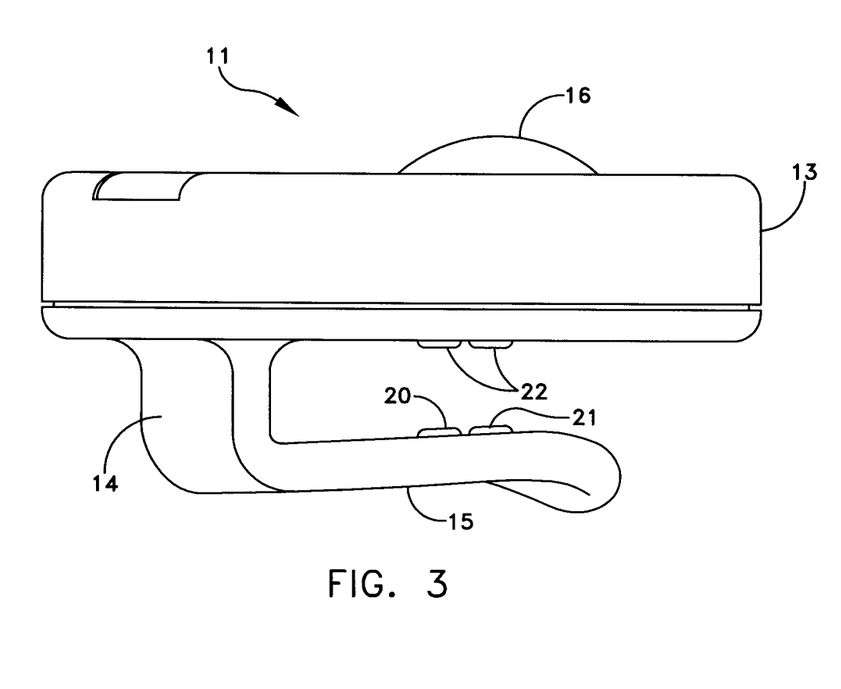

As particularly shown in FIGS. 1 through 3, a sensing-recording device 11 includes a housing or base unit 13, a clip having a transverse portion 14 and a clip arm 15 spaced from and essentially parallel to the housing 13. The housing 13 carries an on/off button 16 as shown in FIGS. 1 and 3 and a portion of a communications link in the form of an IrDA (Infrared Data Association) transceiver located behind window 17 in FIG. 1. The clip arm 15 and housing 13 provide a means for attaching the sensing-recording device 11 to the patient.

Both the housing 13 and arm 15 include sensing elements. In the embodiment shown in FIG. 3 the clip arm 15 carries a dermal phase meter (DPM) electrode assembly 20 that may include a temperature sensor (not shown) and carries a photocell 21. These sensors 20 and 21 connect through conductors embedded in the clip arm 15 and link 14 to circuitry in the housing 13. The housing 13 may include other elements such as light emitting diodes (LED) 22 for generating light in the red and infrared bandwidths for being sensed by the photocell 21 for pulse oximetry as known in the art. It will become apparent that other sensors could be substituted for each or all of these specific sensors or added thereto.

In use a medic will, upon arrival at a patient, attach one sensing-recording device to that patient. For example the sensing-recording device 11 could be attached by sliding the clip arm 15 into the patient's mouth and positioning the housing 13 on the patient's cheek.

Figure 4:
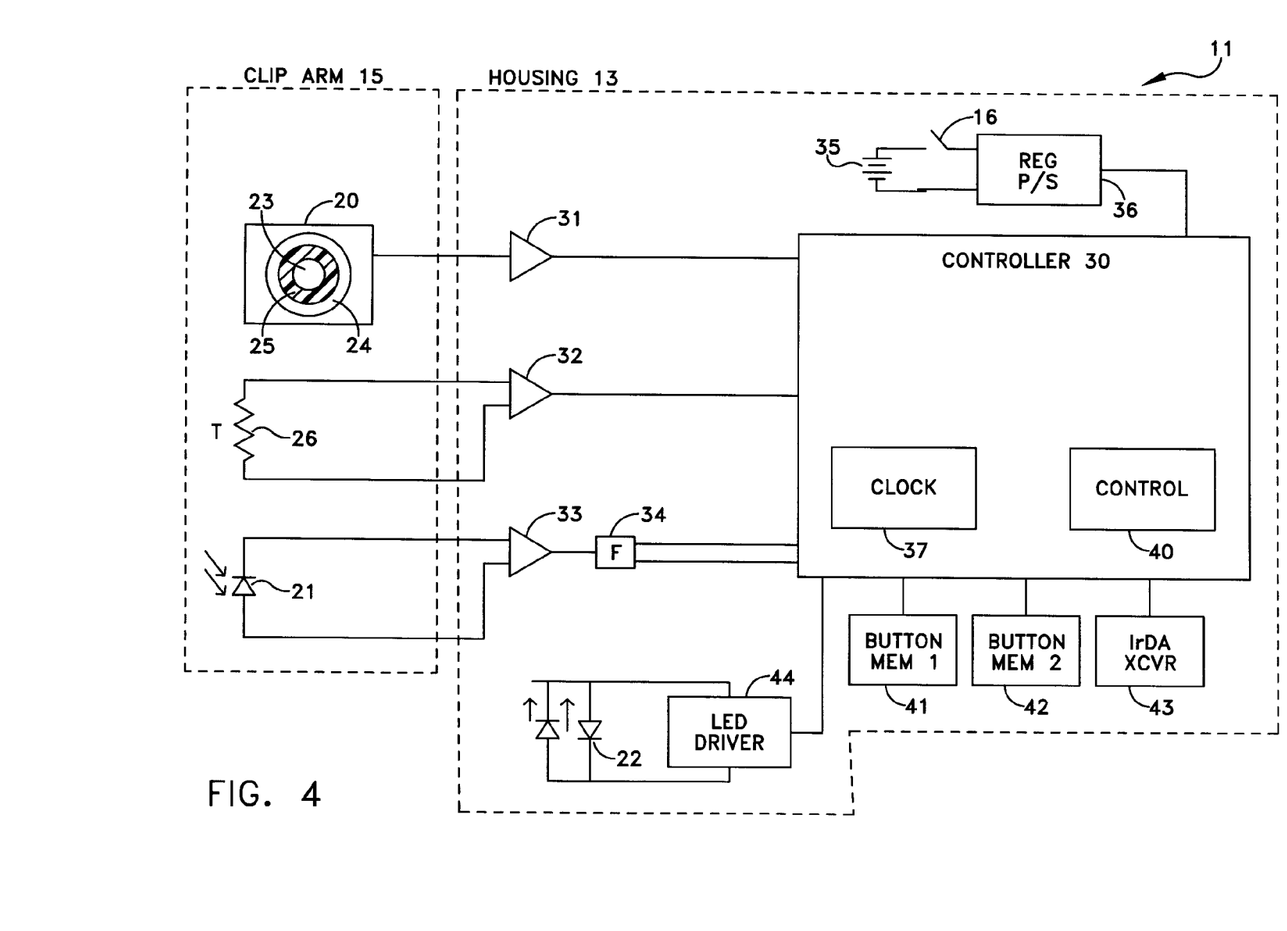
FIG. 4 is a block diagram of the circuitry associated with the sensing-recording device shown in FIGS. 1 through 3.

FIG. 4 is a block diagram of the circuitry of the sensing-recording device 11. As shown, the clip arm 15 includes the DPM electrode assembly 20 with an inner electrode 23, an outer annular electrode 24 and intermediate annular insulator 25.

In this embodiment a temperature sensing element 26 is also included in the clip arm 15. It is shown separately in FIG. 4, but can be incorporated as part of the DPM electrode assembly 20. FIG. 4 also depicts the photocell 21.

Each of these sensors produces a signal that is transferred to a controller 30 located in the housing 13. In this specific embodiment amplifiers 31 and 32 convey amplified analog signals representing skin impedance and temperature to the controller 30. An amplifier 33 and filter 34 provide signals to the controller 30 from the photocell 21 representing specific frequencies of the light emitted by the LEDs 22.

When the on/off switch 16 is closed there is a connection between a battery 35 and a regulated power supply (REG P/S) 36 for energizing the controller 30 with an internal clock 37. A control 40 operates so the controller 30 interacts with memory. In this specific embodiment the memory is partitioned into BUTTON MEM 1 memory 41 and BUTTON MEM 2 memory 42. Other partitioning could also be used. As will become apparent, functionally the memory can be considered as having two partitions. The controller 30 also interacts with the IrDA transceiver 43 that would be located behind the window 17 in FIG. 1.

When a sensing-recording device 11 has been attached to a patient, the medic actuates the on/off switch 16 to energize the controller. As described in more detail later, communications are then established between the probe 12 and the sensing-recording device 11 through the IrDA transceiver 43. When this occurs, the control 40 begins to sample the outputs of the various sensors from the clip arm 15 and activates an LED driver 44 to begin the measurement sampling sequence. The control 40 transfers each sample into the BUTTON MEM 1 memory 41. In a preferred embodiment no sampled data is applied to the BUTTON MEM 2 memory 42. Typically the BUTTON MEM 1 memory 41 will have a capacity to store samples for 12 hours or so and may also act as a FIFO stack.

In response to other communications the control 40 decodes information from the transceiver 43 for being loaded into BUTTON MEM 2 button 42 and for transferring data from the BUTTON MEM 1 button 41 to the probe. The controller 30 also includes circuitry (not shown, but known in the art) for converting signals from the various sensors in the clip arm 15 into digital formats for recording in the BUTTON MEM 1 memory 41.

Each sample is stamped with information from the clock 37. As described later, the time in the clock 37 is established by communications between the probe 12 and the sensing-recording device 11.

Probe 12

Figure 5:
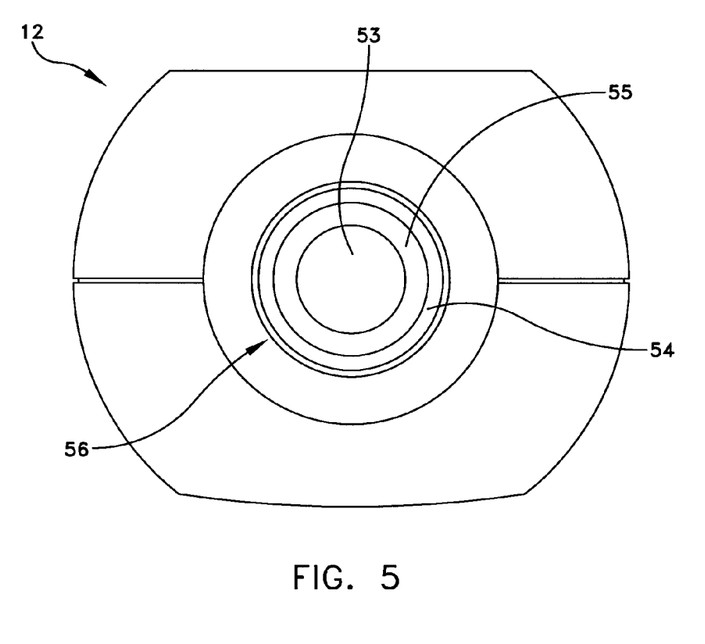
FIGS. 5 and 6 are alternate views of the probe shown in FIG. 1.
Figure 6:
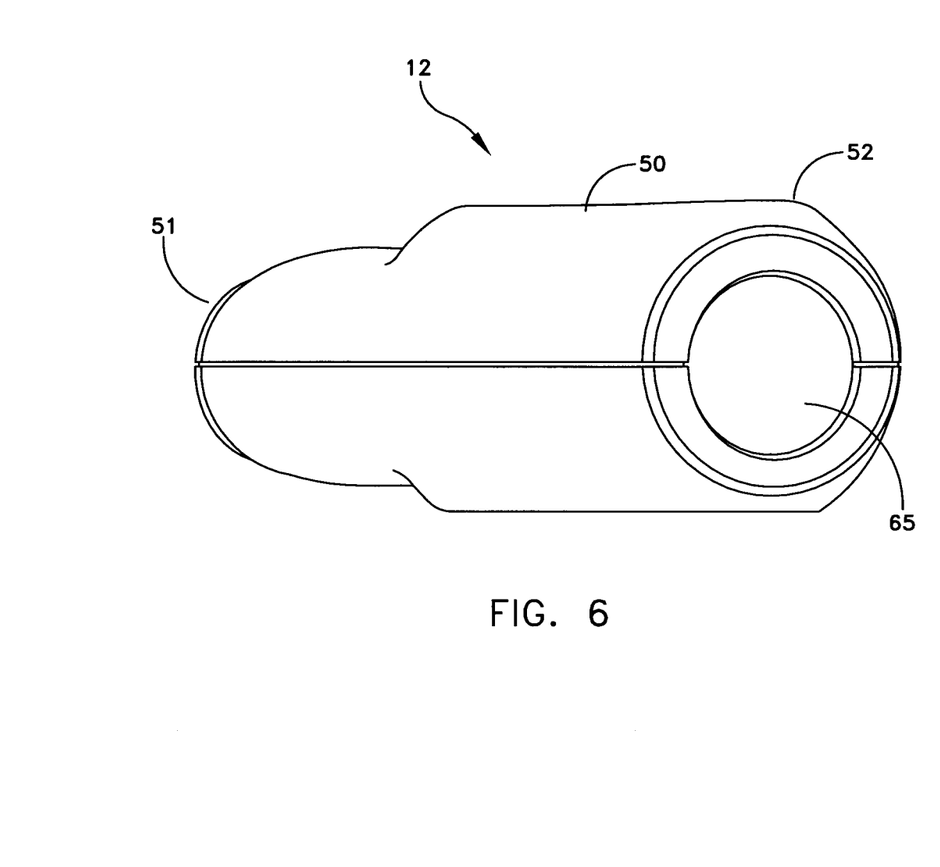

Now referring to FIGS. 1, 5 and 6, the probe 12 has a housing 50 that extends between opposite end portions 51 and 52. The end portion 51 carries concentric conductors 53 and 54 with an intermediate insulator 55 that constitute a probe DPM electrode assembly 56 as shown in FIGS. 1 and 5. This DPM electrode assembly 56 may also include a temperature sensor, not shown in FIGS. 1 and 5.

The housing also includes a digital display 60 proximate the other end portion 52. In this specific embodiment, a first keypad 61 has four scroll buttons for allowing the medic to move information transversely or parallel to the probe axis. Another keypad 62 may include an on/off button 63 and an "ENTER" button 64. Other structures may be substituted.

Referring to FIG. 6, the probe 12 includes an IrDA transceiver, not shown in FIG. 1, 5 or 6, but located behind a window 65 at the end portion 52 of the housing 50 as shown in FIG. 6.

Figure 7:
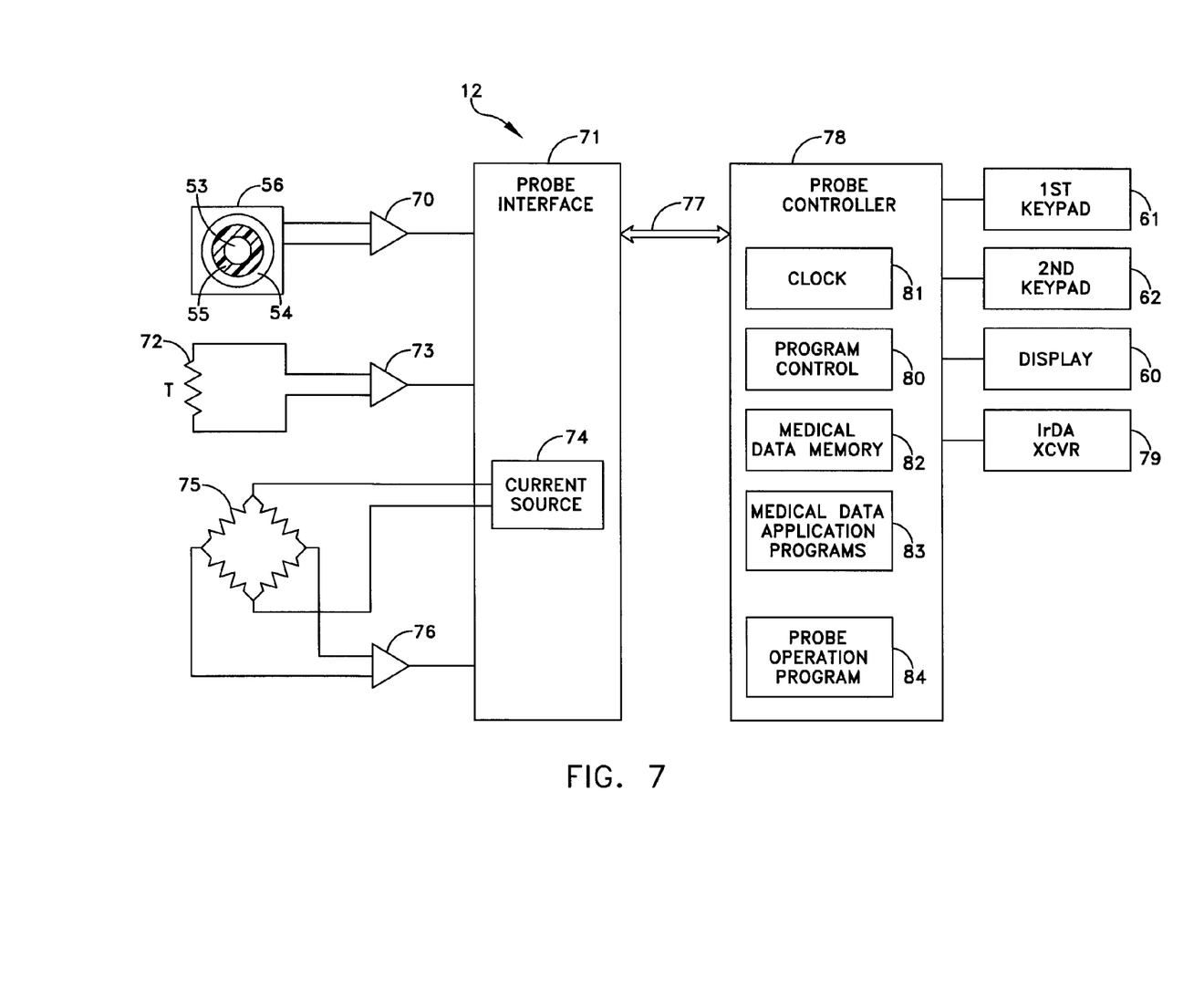
FIG. 7 is a block diagram of the electronic circuitry of the probe of FIGS. 1, 5 and 6.

FIG. 7 depicts one embodiment of control circuit for providing the various probe functions. An amplifier 70 provides signals from the DPM electrode assembly 56 to a probe interface 71. The probe interface 71 also interfaces signals from a temperature responsive element 72 provided by an amplifier 73 and includes a current source 74 for energizing a bridge 75 so an amplifier 76 produces a force measurement signal. The bridge 75 can be collocated with the temperature sensor 72 and DPM electrode assembly 56 as known in the art.

Basically the probe interface 71 converts signals from the various sensors into a digital format for transmission across a path 77 to a computer-driven probe controller 78. The probe controller 78 also interfaces with the first and second keypads 61 and 62, the display 60 and an IrDA transceiver 79 that is located behind the window 65 in FIG. 6.

The probe controller 78 includes a program controlled central processor represented as a program control 80. The probe controller 78 also includes a clock 81 that can be synchronized to any real time through interaction between the display 60 and the keypads 61 and 62. A medical data memory 82 stores any information provided by medical data application programs 83, such as an OMAS program for converting signals from the various sensors attached to the probe interface into an Oral Mucositis Assessment Scale (OMAS) value. The medical application programs 83 produce the data in the medical data memory 82 along with a time stamp based upon information from the clock 81. All these operations occur in response to a probe operation program 84.

Operation

Figure 8:
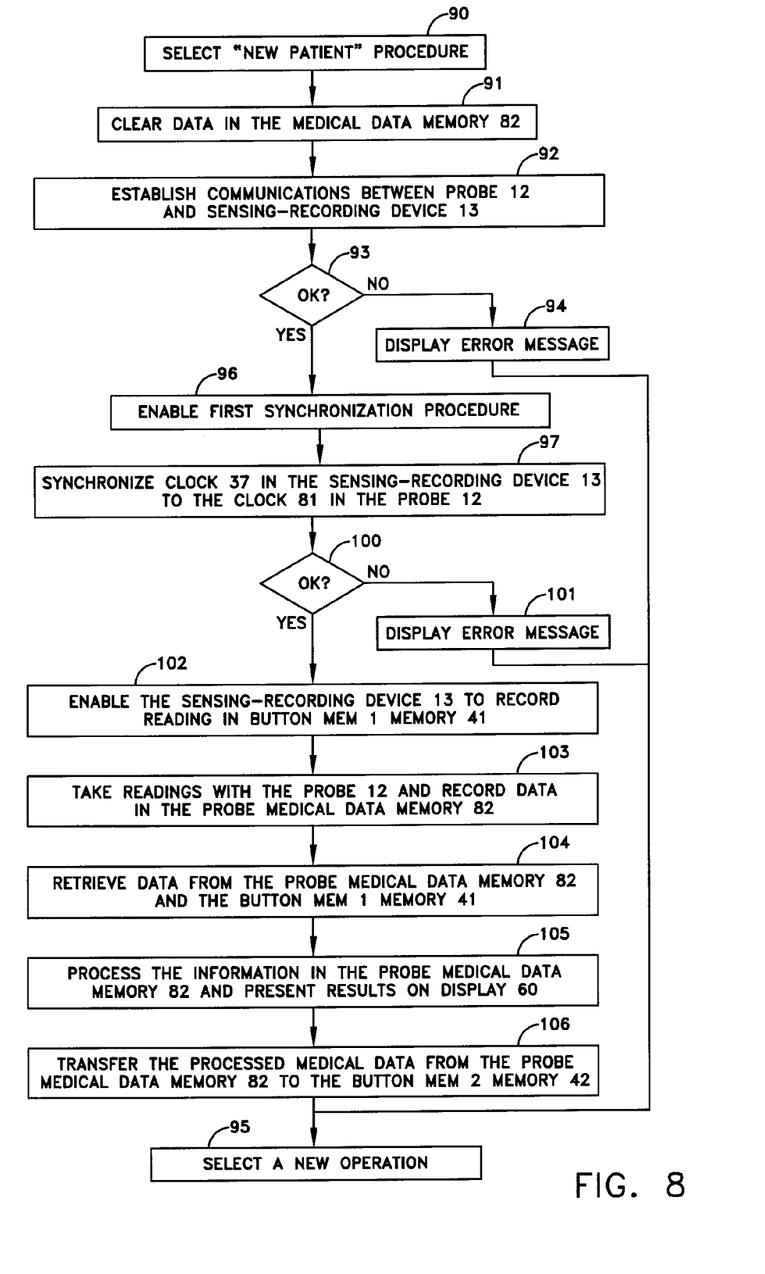
FIG. 8 is a flow diagram that depicts the operation of the probe and interaction with a sensing-recording device.

The probe operation program 84 defines a series of tasks including proposed actions to be displayed through instructions on the display 60 and reactions in response to data received either from the probe interface 71 or the IrDA transceiver 79 or input from the keypads 61 and 62. For example, when a medic approaches a new patient, he might use the first keypad 61 to scroll information on the display to initiate a "NEW PATIENT" procedure in response to actuating the "enter" button 64 in the second keypad 62. A typical operation in response to that selection is shown in FIG. 8 where step 90 represents that selection. Step 91 represents the step of clearing the data from the medical data memory 82 so that the probe contains no data from any prior measurements related to any other patient.

Step 92 then attempts to establish communications between the probe 12 and the sensing-recording device 11 through the IrDA transceiver 79 shown in FIG. 7 and the IrDA transceiver 43 in FIG. 4. Procedures for establishing these communications and procedures for performing each of the other steps will be apparent to those of ordinary skill in the art. If communications are not established step 93 transfers control to step 94 to display an error message on the display 60. That error message may also instruct the medic to divert to another operation program for recovering from the error. Control then transfers to step 95 to enable selection of a task in view of the error or selection of an entirely unrelated task.

Once communications are established, however, control transfers from step 93 to step 96 to enable a first synchronization procedure. Assuming that the medic has energized the sensing-recording device housing 13 by activating the on/off switch 16, one of the steps will be to synchronize the clock 37 in the sensing-recording device 13 shown in FIG. 4 to the clock 81 in the probe controller of FIG. 7. Specifically, the clock 37 will have begun operation at some random time when the on/off switch has been activated. Step 97 allows the synchronization to occur and the clock 37 then to be updated. Typically the clock 37 will then run as accurately or nearly as accurately as the clock 81.

If the synchronization of step 97 can not be completed successfully, step 100 transfers control to step 101 to display an error message 100 and potentially provide information with respect to recovering from the error. Control then transfers to step 95.

Once the clock synchronization has occurred, the program operation control uses step 102 to communicate through the IrDA transceivers 79 and 43 in FIGS. 7 and 4 and enable the sensing-recording device 11 to record readings in the BUTTON MEM 1 memory 41. Step 103 represents a process during which a medic can use the probe 12 to take additional readings independently using the medical data application program 83 with recorded results being in the probe medical data memory 82. These readings may also be under control of the program with appropriate displays specifying specific tasks to be taken.

When the medic has completed actions in step 103, step 104 is initiated. Step 104 represents the process by which the medic initiates the retrieval of information from the BUTTON MEM 1 memory 41 that contains the time stamped data relating to the monitoring operation by the sensing-recording device 11. When all the data has been retrieved, step 105 processes the information in the probe medical data memory 82, including the information from the BUTTON MEM 1 memory 41, to produce results as feedback to the medic according to medical data application programs 83. For example, one display might be a graphical representation of OMAS values over a period of time. During this interval, the sensing-recording device 11 continues to add data to the BUTTON MEM 1 memory 41.

When step 105 completes its operations, step 106 transfers selected data from the medical data memory 82 to the BUTTON MEM 2 memory 42. Thus the BUTTON MEM 2 memory 42 contains all the results of the readings taken by the medic at the battlefield site and the results of any data that was contained in the BUTTON MEM 1 memory 41 that was processed in step 105. When step 106 is completed, control transfers to step 95 to select a new operation.

Thus, when the patient is transported, the sensing-recording device 11 contains data in the BUTTON MEM 2 memory 42 that identifies his condition when the medic attended the patient. The BUTTON MEM 1 memory 41 contains the time stamped raw data that continues to be obtained from the various sensors in the sensing-recording device 11.

When the patient reaches a medical facility, it is a simple matter for a properly equipped data processing system, such as a laptop computer with an IrDA port, to communicate with the controller 30 in the sensing-recording device 11 and download all the data from both the BUTTON MEM 1 memory 41 and the BUTTON MEM 2 memory 42. This data can be further processed in accordance with various application programs to provide further diagnostic information. Unlike the prior art, however, this information provides a continuum of patient data from the time first synchronization procedure is initiated until the time the data is downloaded from the patient.

As will now be apparent, apparatus constructed in accordance with this invention and based upon the specific embodiment shown in FIGS. 1 through 7 provides patient monitoring apparatus that is adapted for use in a variety of environments including battlefield environments. This patient monitoring apparatus is easy to use and facilitates the measurement of diverse physiological parameters. Moreover, the apparatus enables the monitoring of these parameters from the arrival of a medic or a first responder at the patient to the arrival of the patient at a medical facility.

It will also be apparent that this invention has been described with respect to a specific embodiment with particular organization of components and controls. A number of variations can be made by those of ordinary skill in the art without departing from this invention. For example, the sensing-recording device 11 is shown with a structure particularly suitable for disposing the sensing-recording device housing 13 on a patient's cheek with the clip arm 15 within the mouth. This structure non-invasively attaches the sense-recording device 11 to the patient. Other form factors could be utilized that would adapt the function of the sensing-recording device 11 for attachment to other parts of the body, such as an earlobe, as might be dictated by a particular set of physiological parameters being measured. The probe 12 has been shown as a single device with particular form factor and layout of controls. Each of those could be modified to adapt the probe to different ergonomic or other conditions.

Similarly FIGS. 4 and 7 depict particular embodiments of the electronics carried within the sensing-recording device housing 13 and probe housing 50. Different sensors could be substituted for any of the specifically disclosed sensors. Different memory organizations could be utilized.

Communications using mechanisms other than IrDA transceivers could be used. The organization of a control, such as the control 40 in FIG. 4 and the program control 80 in FIG. 7 could be changed. FIG. 7 depicts probe interface 71 and a probe controller 78. In other embodiments the functions of these two elements could be combined in a single unit. Consequently it is the intent to claim this invention to cover this particular embodiment and any equivalent embodiments that may be developed.

What is claimed as new and desired to be secured by Letters Patent of the United States is:

1. A patient monitoring apparatus for measuring medical parameters of a patient initially at a site remote from a medical facility and during transport of a patient to the medical facility, said apparatus including a sensing-recording device, a probe and communication means for establishing communications between said sensing-recording device and said probe wherein:

A) said probe comprises:
i) a probe memory,
ii) sensor means for generating at least one parameter signal representing at least one medical parameter for the patient,
iii) means for processing said at least one parameter signal for storage in the memory, and
iv) a probe controller for generating commands to said sensing-recording device to initiate measurement functions therein and to store data in said probe memory from a sensing-recording device over the communications means, and B) said sensing-recording device comprises:
i) a housing,
ii) a clip arm extending from said housing for non-invasively attaching said sensing recording device to a patient during examination at the remote site and during transport to the medical facility,
iii) at least one sensor carried by said clip arm for generating at least one parameter signal that represents at least one medical parameter for the patient, one of said sensors being a sensor for pulse oximetry and including a photocell in said clip arm and a light emitting diode carried in said housing,
iv) a memory in said housing, and
v) a control in said housing that stores samples of the parameter output for each of the at least one sensor in said sensing-recording device memory and responds to a first command from said probe by transferring data in said sensing-recording device memory to said probe memory and to a second command from said probe by transferring data from said probe memory to said sensing-recording device memory whereby said sensing-recording device contains all the information obtained at the remote site and continues to record information independently of said probe during the transport of the patient to the medical facility.

2. The patient monitoring apparatus as recited in claim 1 wherein said communication means comprises a transceiver in said probe and a transceiver in said sensing-recording device, said transceivers establishing an optical communications path between said probe and said sensing-recording device.

3. The patient monitoring apparatus as recited in claim 2 wherein said probe includes input means for entering data into said memory for controlling the operation of said probe and includes an operation control for responding to the initiation of recording for a new patient by clearing said memory in said probe.

4. The patient monitoring apparatus as recited in claim 3 wherein said sensing-recording device includes a clock and means for time-stamping each sample recorded in said device memory and said probe includes a clock, said operation control further responding to the initiation of recording for a new patient by synchronizing the clock in said device to the clock in said probe whereby said memory in said device stores a continuum of data for the patient.

5. The patient monitoring apparatus as recited in claim 3 wherein said probe includes means for sensing medical parameters and means for storing the samples of said parameter in the probe memory, said probe controller processing the data from the memories in the probe and said sensing-recording device.

6. The patient monitoring apparatus as recited in claim 5 wherein said memory in said sensing-recording device includes first and second memories and said probe controller transfers the processed data to said second memory while said first memory continues to record patient data generated by said sensors.

7. The patient monitoring apparatus as recited in claim 1 wherein one of said sensors carried by said clip arm is a dermal phase meter.

8. The patient monitoring apparatus as recited in claim 1 wherein one of said sensors carried by said clip arm is a temperature sensor.

9. The patient monitoring apparatus as recited in claim 1 wherein said probe includes:
   i) at least one sensor for monitoring physiological parameters for storage in said probe memory,
   ii) display means, and
   iii) means in said processing means for generating a display for viewing on said display means.

10. The patient monitoring apparatus as recited in claim 9 wherein said memory in said sensing-recording device housing comprises first and second memories and said probe controller transfers the processed data to said second memory while the first memory continues to record patient data generated by said sensor.

11. A patient monitoring system adapted for use by medical personnel at a trauma site that is remote from a medical facility comprising:
   A) a plurality of sensing-recording devices, each including:
      i) a housing,
      ii) a clip arm extending from said housing whereby a said sensing-recording device is attached to a patient non-invasively at the trauma site for transport to the medical facility,
      iii) at least one sensor carried by clip arm, each of said at least one sensor generating a signal that represents a medical parameter, one of said sensors of said sensing-recording device including a sensor for pulse oximetry including a photocell in said clip arm and a light emitting diode carried in said housing,
      iv) first and second memories,
      v) a controller for storing time-stamped data sample entries for each sensor in said sensing-recording device in said first memory,
      vi) transceiver means for establishing communications over an optical communications path, and
      vii) means for conveying information from said transceiver means to said second memory, and
   B) a probe including:
      i) a plurality of sensors, each sensor generating a signal that represents a medical parameter,
      ii) a memory,
      iii) means for generating time-stamped data entries representing samples of the signal from each sensor in said memory,
      iv) display means,
      v) means for processing the data in said memory for viewing on said display means,
      vi) a keypad,
      vii) a probe operation control that processes a plurality of tasks,
      viii) means for responding to said keyboard for initiating processing of a task from said probe operation control,
      ix) transceiver means for establishing communications over an optical communications path, and
      x) means for conveying information from said probe memory in to said second memory to a said sensor-recording device whereby said sensing-recording device contains all the information obtained at the remote site and continues to record information independently of said probe during the transport of the patient to the medical facility.

12. The patient monitoring apparatus as recited in claim 11 wherein another of said sensors carried by said clip arm is a dermal phase meter.

13. The patient monitoring apparatus as recited in claim 11 wherein another of said sensors carried by said clip arm is a temperature sensor.

* * * * *